United States Patent [19]
Carlhoff et al.

[11] Patent Number: 5,702,550
[45] Date of Patent: Dec. 30, 1997

[54] PROCESS FOR TIRE MANUFACTURE WITH ON-LINE DETERMINING OF CARBON BLACK CONCENTRATION AND DISTRIBUTION IN RUBBER COMPOUNDS AND OTHER CARBON BLACK CONTAINING MATERIALS

[75] Inventors: Christoph Carlhoff, Willich; Martin Jogwich; Claus-Jürgen Lorenzen, both of Essen, all of Germany; Marco Nahmias, Milan, Italy

[73] Assignee: Pirelli Coordinamento Pneumatici S.p.A., Milan, Italy

[21] Appl. No.: 619,411

[22] Filed: Mar. 21, 1996

Related U.S. Application Data

[62] Division of Ser. No. 288,254, Aug. 11, 1994, Pat. No. 5,537,207.

[30] Foreign Application Priority Data

Aug. 13, 1993  [EP]  European Pat. Off. ......... 93113036.3

[51] Int. Cl.$^6$ ..................................................... B29D 30/00
[52] U.S. Cl. ........................... 156/64; 156/110.1; 156/123
[58] Field of Search .................................. 356/317, 318; 156/64, 110.1, 123, 133; 524/495, 496; 73/146; 366/69

[56] References Cited

U.S. PATENT DOCUMENTS

| | | |
|---|---|---|
| 4,076,220 | 2/1978 | Nakashima et al. ............ 366/69 |
| 4,301,411 | 11/1981 | Wardell et al. . |
| 4,641,968 | 2/1987 | Grandy . |

FOREIGN PATENT DOCUMENTS

| | | |
|---|---|---|
| 40 04 627 A1 | 2/1991 | Germany . |
| 2043262 | 10/1980 | United Kingdom . |

OTHER PUBLICATIONS

English language abstract for DE 4004627, Derwent Information Ltd, Feb. 1991.

Time–Resolved Laser–Induced Breakdown Spectroscopy of Iron Ore; K. J. Grant, G.L. Paul, and J. A. O'Neill; 1369 Applied Spectroscopy 44 (1990) December , No. 10, Frederick, MD, US.

Materials analysis using laser-based spectrscopic techniques' B.J. Goddard, BSc,PhD, 2190a Transactions of the Institute of Measurement and Control; 13 (1991) No. 3 London, GB.

*Primary Examiner*—Geoffrey L. Knable
*Attorney, Agent, or Firm*—Griffin, Butler Whisenhunt & Kurtossy

[57] ABSTRACT

To determine the carbon black distribution two measurements of spectral intensities of separately produced plasmas are carried out with different time delays relative to a particular laser pulse, the time delay for the second measurement for determining the spectral line intensities of a reference element carbon ($I_C$) and at least one analysis element ($I_{A,n}$) being smaller than for the first measurement; for determining the spectral line intensities of the reference element ($I_C$) and the other analysis elements ($I_{A,n}$).

Evaluation of the measurements is performed by reference to calibration information based on reference measurements, which information shows the magnitude of the concentration ratio of the other analysis elements or the at least one analysis element to the reference element ($c_{A,n}/c_C$ or $c_{A,n}/c_R$) as a function of the appurtenant intensity ratio values. By comparison between the intensity ratio values from both measurements with the calibration information, using the concentration of total carbon ($c_C$) and that of the selected analysis element ($c_{A,n}$), the magnitude of the carbon black concentration ($c_R$) is determined.

3 Claims, 4 Drawing Sheets

PROCESS FOR TIRE MANUFACTURE WITH ON-LINE DETERMINING OF CARBON BLACK CONCENTRATION AND DISTRIBUTION IN RUBBER COMPOUNDS AND OTHER CARBON BLACK CONTAINING MATERIALS

This is a divisional application of Ser. No. 08/288,254 filed Aug. 11, 1994 now U.S. Pat. No. 5,537,207.

BACKGROUND OF THE INVENTION

This invention concerns a process for determining the carbon black concentration and distribution in rubber compounds and other carbon black-containing materials using pulsed laser beams focused on the material surface each of which produce a plasma with a radiation characteristic of the elements or molecules contained therein and divide the surface with their end regions into grid areas in which are located measuring points formed by the laser beam focuses, whereby the characteristic radiation, spectrally dispersed in the form of spectral lines or molecule bands, is measured by a detector unit and whereby from the concentration values calculated by reference to numerical ratios from the radiation intensities of selected elements/molecules with subsequent storage and allocated to the relevant measuring points, the concentration value curve at least over a section of the surface is established.

In one aspect, the present invention lies in having perceived, as an essential part of a tire manufacturing process, the technical problem of measuring the carbon (C) associated with the carbon black separate from the carbon of the rubber material, particularly and preferably based on different responses to ignition.

According to this aspect, the invention also concerns a process for manufacturing a pneumatic tire for vehicle wheels, substantially comprising the steps of preparing rubber compounds for a plurality of semi-finished components, of preparing semi-finished components from said compounds and of assembling together said components in a raw carcass, according to which the elemental carbon from carbon black contained in at least one of said compounds, or semi-finished components, is quantitatively detected on-line, thus monitoring in real time the dispersion degree and the homogeneity of the carbon black in said at least one rubber compound, so as to control and, if needed, to vary, on the basis of said detected information, the quantity of carbon black which is going to be mixed with polymeric materials and other ingredients for preparing said at least one rubber compound.

The invention relates further to a suitable device to perform the process for determining the carbon black concentration and distribution in rubber compounds and other carbon black-containing materials, comprising a facility for producing briefly maintained laser beams, a first optical assembly lying in their axis consisting of a first lens arrangement and a first deflector unit for aligning the laser beam end regions—whose laser beam focuses in each case form a measuring point—relative to the material surface, a second optical assembly with a second lens arrangement exhibiting a second deflector unit, by which second lens arrangement the radiation from the plasma produced in the laser beam focus can be supplied to a spectrograph with detector unit to identify the radiation constituents, and a computer serving as evaluator connected with the detector unit, whereby the plasma is evaluated before the next laser pulse is actuated and from the concentration values stored in the computer— which have been calculated by comparison with corresponding ratios from specimens of known composition by reference to numerical ratios from the measured radiation intensities of selected elements/molecules and are assigned to various measuring points—the concentration value curve at least over a section of the surface is established.

A process and a device of the above mentioned kind are known from DE-A1-40 04 627; there, the surface to be examined is divided by a relative movement between itself and the end region of the laser beam into grid areas which are each assigned to a measuring point formed by the laser beam focus. To be able to gain information on the degree of mixing and the degree of concentration and dispersion of the constituents contained in the material, the number of measuring points in one section of the surface can be adjusted in several gradations by altering in a suitable way the pulse frequency of the laser unit and/or the movement of the measuring point. Depending on whether it is intended to examine the degree of overall material homogeneity or the degree of dispersion on the surface, the spacing between the measuring points assigned to the grid areas is relatively large or relatively small; this difference is due to the fact that the aim of investigating the degree of dispersion is to gain information on fine, small-area constituents such as for example salt crystals.

Underlying the invention is the task of configuring the known process and the known device—which are based on the TRELIBS principle (Time-Resolved Laser-Induced Breakdown Spectroscopy)—in such a way that the concentration and distribution of carbon black in rubber compounds and other carbon black-containing materials, particularly in tire compounds, can also be determined.

It is known that in making vehicle tires a raw carcass is first provided, which carcass is achieved by successively assembling together several different semi-finished components consisting of rubberized fabrics, reinforced with textile or metallic cords, and total rubber components.

By way of example, when the carcass for a tubeless tire is to be produced, that is a carcass for tires that in use do not require the presence of an inner tube, the main components include a so-called "liner", that is a layer of elastomeric air-proof material, a carcass ply, a pair of annular metal elements, commonly referred to as bead cores, around which the opposite ends of the carcass ply are folded, as well as a pair of side pieces made of elastomeric material, which will constitute the sidewalls of the tire, extending over the carcass ply at laterally opposite positions.

The thus assembled carcass is then submitted at least to the application of a so-called "belt pack" and of a tread band, provided for being imprinted with an appropriate tread pattern: the completed raw tire is then ready for undergoing the final vulcanization process for the purpose of obtaining a finished tire.

The process to make the raw carcass, substantially starts with the step, made in a so-called bambury, of preparing a rubber compound by mixing together at least a polymeric material with other ingredients, including carbon black, according to prefixed quantitative ratios between said ingredients established in a given recipe; subsequently, from said compound at least a semi-finished component for said tire is formed, like the tread band or the sidewalls or other rubber components.

In a process "of continuous type" the forming devices, like the extruders or calendars and so on, quite conveniently, are directly feeding the tire building apparatus, on which a plurality of said semi-finished components are assembled together to build up a raw carcass, subsequently molded and vulcanized in a curing mold.

The advantage of this kind of process is that to minimize the need to store and manage a lot of semi-finished components, thus avoiding storage costs and possible problems in respect of feeding the requested components to the tire building apparatus. It is then easy to appreciate the importance to check and measure, as soon as possible, and in real time during said building process, the composition of the corresponding compounds, i.e. the concentration and the degree of dispersion of the various ingredients, including the carbon black, in said compounds.

A check on the semi-finished components coming from a store, Just before their assembling in the raw carcass, or during their manufacture according to said continuous process, notwithstanding is possible, in case a wrong composition of the related compounds should be detected, would require to restart with the preparation of said rubber compounds and the corresponding components, with waste of time and money, and possible great disadvantages on the flow of the semi-finished components during the tire building process.

Accordingly, the preferable time and place at which to have said check done is just when and where the compound is coming out of the bambury: by this way it is possible to immediately vary, on the basis of said detected information, the quantity of carbon black and other ingredients which are going to be loaded in the bambury to be mixed with said polymeric materials so as to fit the established composition for said compounds according to the prefixed quantitative ratios of ingredients of the given recipe, thus avoiding the preparation of possible batches of rubber compounds and/or a lot of semi-finished components not respondent to the prescribed provision.

In the following we will call as "on-line process" a manufacturing process in which the control on the product is made during the process. In the above, it has been proved to be of the greatest importance to check the concentration and distribution of the carbon black content in said tire rubber compounds.

The carbon black content influences above all the material hardness of such rubber compounds and therefore provides information on certain properties and the quality of the rubber compound to be examined. Determining the carbon black content has hitherto proved difficult insofar as this constituent can only be measured indirectly and only through laboratory tests, not allowed in an on-line process. Thus, it is an object of this invention to provide a device and process for measuring directly carbon black in an on-line process.

SUMMARY

This object is achieved by a process and device involving determining a carbon black distribution and concentration in rubber compounds and other carbon black-containing materials using pulsed laser beams focused on a material surface, each of which produces a plasma with a radiation characteristic of the elements or molecules contained therein and divides the surface with its end region into grid areas in which are located measuring points formed by the laser beam focuses. A characteristic radiation, dispersed spectrally in the form of spectral lines or molecule bands, is identified by a detector unit. From concentration values, which are calculated by reference to numerical ratios from radiation intensities of selected elements/molecules (with subsequent storage thereof) and which are allocated to relevant measuring points, a concentration value curve at least over a section of the surface is established.

In this invention the plasmas or plasma groups produced by the two laser pulses, or laser pulse groups, are evaluated by way of two measurements of spectral intensities, namely a first measurement for the first plasma, or the first plasma group, and a second measurement for the second plasma, or the second plasma group. Each of the two connected measurements (related to actuation of the particular laser pulse) is carried out with a fixed, different time delay ($t_{v1}$, $t_{v2}$) relative to a respective time of actuation.

By way of the first measurement, the intensities of the spectral lines of carbon as reference element ($I_C$), and at least approximately all other analysis elements ($I_{A,n}$) in the surface section, are determined and from these the appurtenant intensity ratios ($I_{A,n}/I_C$) of the spectral line of each analysis element to the spectral line of the reference element are determined.

By way of the second measurement, the intensities of the spectral lines of the reference element ($I_C$), and of at least one of the other analysis elements ($I_{A,n}$), are determined and from these the appurtenant intensity ratio is determined, this measurement being carried out with a shorter delay time than the appurtenant first measurement.

By means of calibration curves obtained by reference to specimens of known composition, and by measurements with the time delay of the first measurement, the intensity ratio values ($I_{A,n}/I_C$) from the first measurement are used to determine the values of appurtenant concentration ratios ($c_{A,n}/c_C$) of substantially all analysis elements in the particular surface section and from them the value for the concentration of the reference element ($c_C$) is determined, from which the magnitude of the concentration ($c_{A,n}$) of individual analysis elements can be derived.

By means of at least one further calibration curve obtained by reference to specimens of known composition and by measurements with the time delay of the second measurement the appurtenant intensity ratio value ($I_{A,n}/I_C$) from the second measurement is used to determine the value of the concentration ratio between carbon black ($c_R$) and the particular analysis element ($c_{A,n}$) and taking into account the previously calculated magnitude of the concentration of the analysis element the magnitude of the carbon black concentration is derived.

BRIEF DESCRIPTION OF THE DRAWINGS

The invention is described and explained in more detail below using the embodiments shown in the drawings. The described and drawn features, in other embodiments of the invention, can be used individually or in preferred combinations. The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DESCRIPTION OF THE PREFERRED EMBODIMENT

Figure 1:
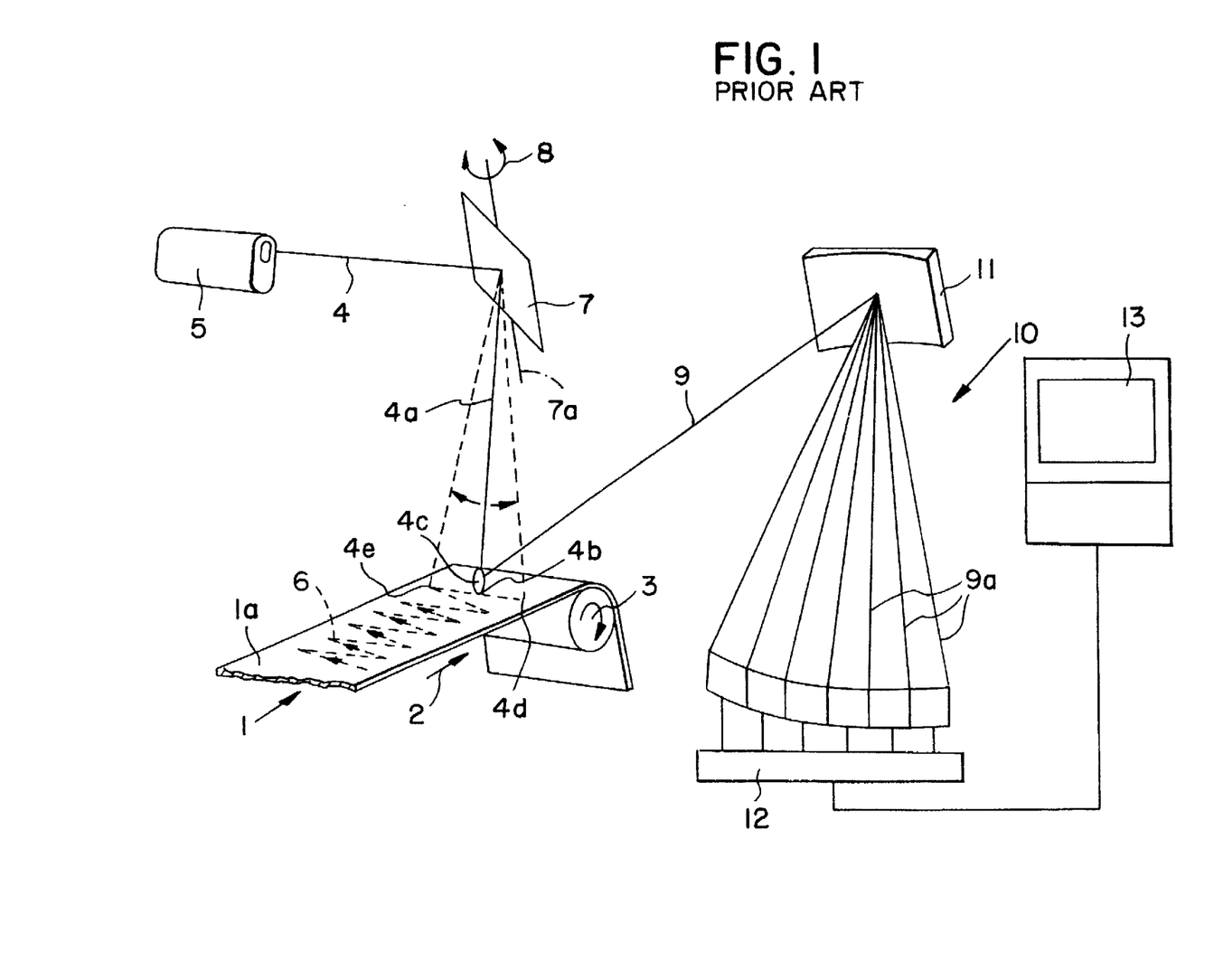
FIG. 1 is a schematic isometric sketch illustrating a fundamental mode of operation of a process of the invention and a fundamental design of a device suited to its performance.

The embodiment example of the invention depicted in FIG. 1 shows a so-called rubber slab 1 being examined to determine also the carbon black concentration contained in its surface, which rubber slab, in the shape of a 1 m wide and 10 mm thick strip leaves the not shown extruder of a rubber mixing plant at a speed of 20 m/min in the direction of arrow 2 and bears on a deflector drum 3.

Such rubber slabs, which are used as semifinished products in the manufacture of vehicle tires, are generally composed of the following constituents:

| Carbon black/carbon: | 40% to 80% |
|---|---|
| ZnO: | 1% to 10% |
| stearic acid: | 0 to 4% |
| silica or silicate: | 0 to 20% |
| sulphur: | 0 to 6% |
| plasticizers: | 0 to 40% |
| other constituents: (for example Co salts, antioxidants, etc.) | 1 to 10% |
| other fillers: (different than carbon black or silica) | 0 to 50% |

Important elements clearly assigned to the stated constituents are S, Zn, Ca, Si and Co; other such elements occurring in almost all constituents are N, H and O as well as carbon, with carbon representing the most frequently occurring matrix element. From the presence of these elements for example conclusions can therefore be drawn as to how the rubber slab to be examined is made up of the above mentioned constituents. According to the present embodiment example the end region 4a of a laser beam 4 emitted by a pulsed laser unit 5 is moved relative to the rubber slab i in such a way that the latter's surface 1a is divided into adjacent grid areas in each of which is located a measuring point 4b formed by the laser beam focus. The movement of the end region 4a transverse to the longitudinal extension of the rubber slab 1—indicated by a broken zigzag line 6—is actuated by a deflector mirror 7; the latter performs a swivelling movement in the direction of the double arrow 8 about a swivel axis 7a. The plasma 4c occurring at each measuring point produces a radiation 9 characteristic of the elements or molecules contained in the plasma, which radiation is supplied to a spectrograph 10 in a way to be described. In the spectrograph the plasma radiation is spectrally dispersed by means of a grating 11 and is identified in the form of individual spectral lines 9a (or possibly in the form of molecular bands) in time-staggered manner by a detector unit 12 configured as a diode array. The digitized spectrum is then transferred to a computer 13 for storage and evaluation.

By reference to calibration curves obtained using specimens of known composition the intensity values obtained from the plasma radiation of each examined measuring point 4b are used to determine the concentration of carbon and selected analysis elements in the surface and from that the appurtenant carbon black concentration.

In detail, to determine the carbon black distribution in the rubber slab 1 the plasmas produced by two laser pulses or laser pulse groups are evaluated by way of two measurements of spectral intensities, namely by way of a first measurement for the first plasma or the first plasma group and a second measurement for the second plasma or the second plasma group, the two connected measurements—related to the actuation of the particular laser pulse—being carried out in each case with a fixed, different time delay $t_{V1}$ and $t_{V2}$ relative to the particular actuation time; in the present embodiment example the delay times are $t_{V1}=1$ μs for the first measurement and $t_{V2}=0.2$ μs for the second measurement.

By way of the first measurement the intensities of the spectral lines of carbon as reference element, or constituents, ($I_C$) and those of all other analysis elements, or constituents, ($I_{A,n}$) in the particular surface section are determined and from these the appurtenant intensity ratios ($I_{A,n}/I_C$) of the spectral line of each analysis element to the spectral line of the reference element are determined.

By way of the second measurement the intensities of the spectral lines of the reference element ($I_C$) and at least one of the other analysis elements ($I_{A,n}$) are determined and from them in each case the appurtenant intensity ratio is determined.

The exposure times $t_{B1}$ and $t_{B2}$ of the detector, during which the produced plasma is observed and analyzed in the performance of the first and second measurements, are 10 μs and 0.2 μs respectively.

The quantitative evaluation of the results of the first and the second measurements is carried out by reference to the calibration information in calibration curves obtained from standard specimens, i.e. from specimens of known composition, using the delay times $t_{V1}$ and $t_{V2}$ and the exposure times $t_{B1}$, $t_{B2}$ of the first and second measurements.

The calibration curves show the magnitude of the previously mentioned intensity ratios $I_{A,n}/I_C$ of the spectral line of each analysis element to the spectral line of the reference element and the intensity ratio $I_C/I_{A,n[40]}$ of the spectral line of the reference element to the spectral line of the at least one selected analysis element as a function of the appurtenant concentration ratio values $c_{A,n}/c_C$ and $C_R$ (for the carbon black concentration)/$c_{A,n}$. In general for the two groups of calibration curves the relations:

$$I_{A,n}/I_C = f(c_{A,n}/c_C) \text{ and } I_C/I_{A,n} = f(c_R/c_{A,n}) \text{ apply.}$$

Figure 2:
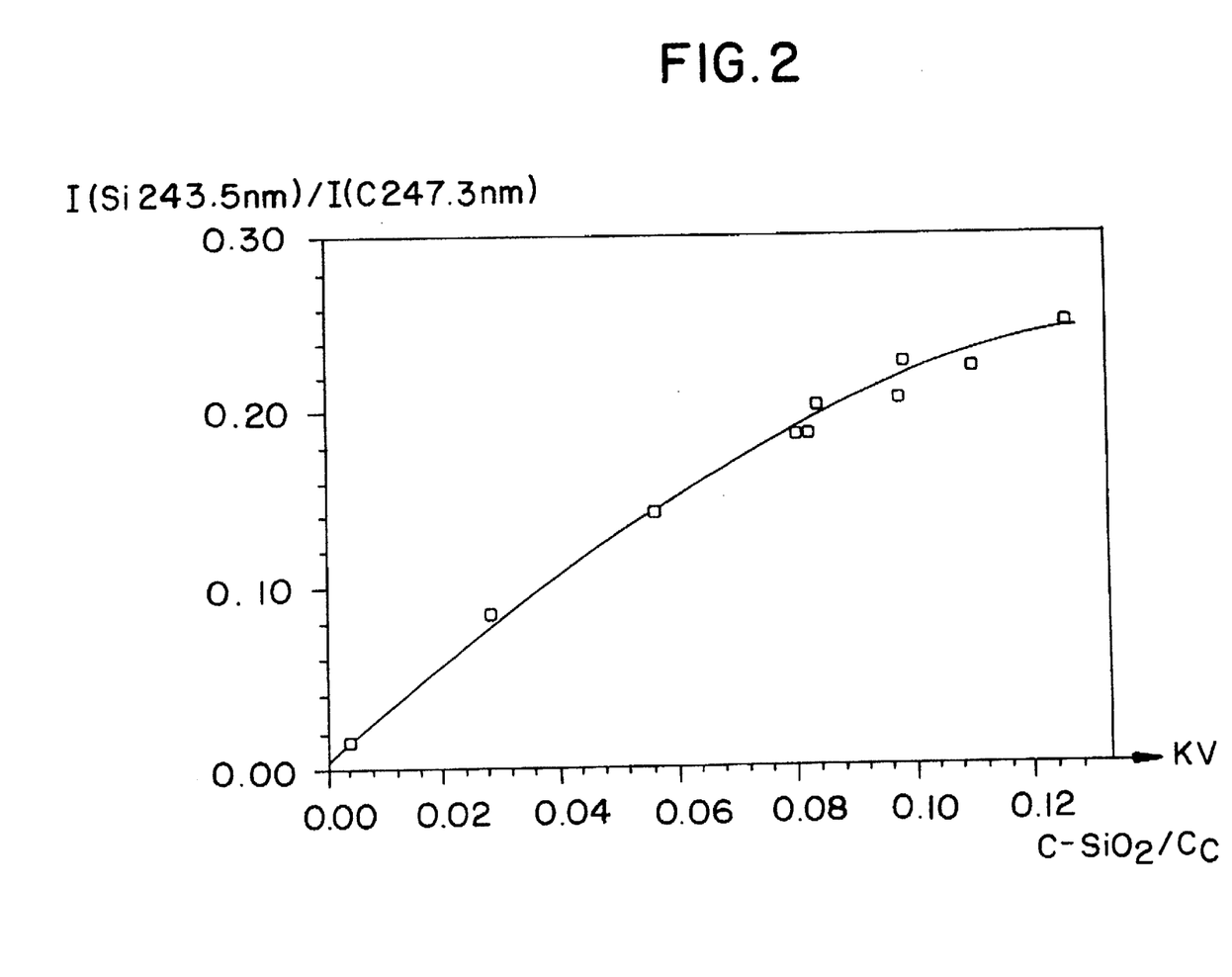
FIG. 2 is a graphic plot showing, by way of example, a calibration curve with carbon as reference element and silicon as analysis element, which curve was determined by reference to specimens of known composition and is used in a quantitative evaluation of a first measurement of this invention.

As an example FIG. 2 shows a calibration curve which indicates for the analysis element Si (spectral line Si=243.5 nm) and the reference element C (spectral line C=247.9 nm) the relationship between the appurtenant intensity ratio values and concentration ratio values KV (c-SiO$_2$/c$_C$); corresponding calibration curves show the relationship between intensity ratio values and concentration ratio values of all other analysis elements contained in the surface section. By comparison between the intensity ratio values of the first measurement and those of the appurtenant calibration curves the appurtenant concentration ratio values can be determined and from these, subject to the condition that the concentration values of all analysis elements and the reference element amount to 100%, the concentration value $c_C$ of carbon and where applicable also the concentration values of selected or of all other analysis elements $c_{A,n}$ can be derived.

Figure 3:
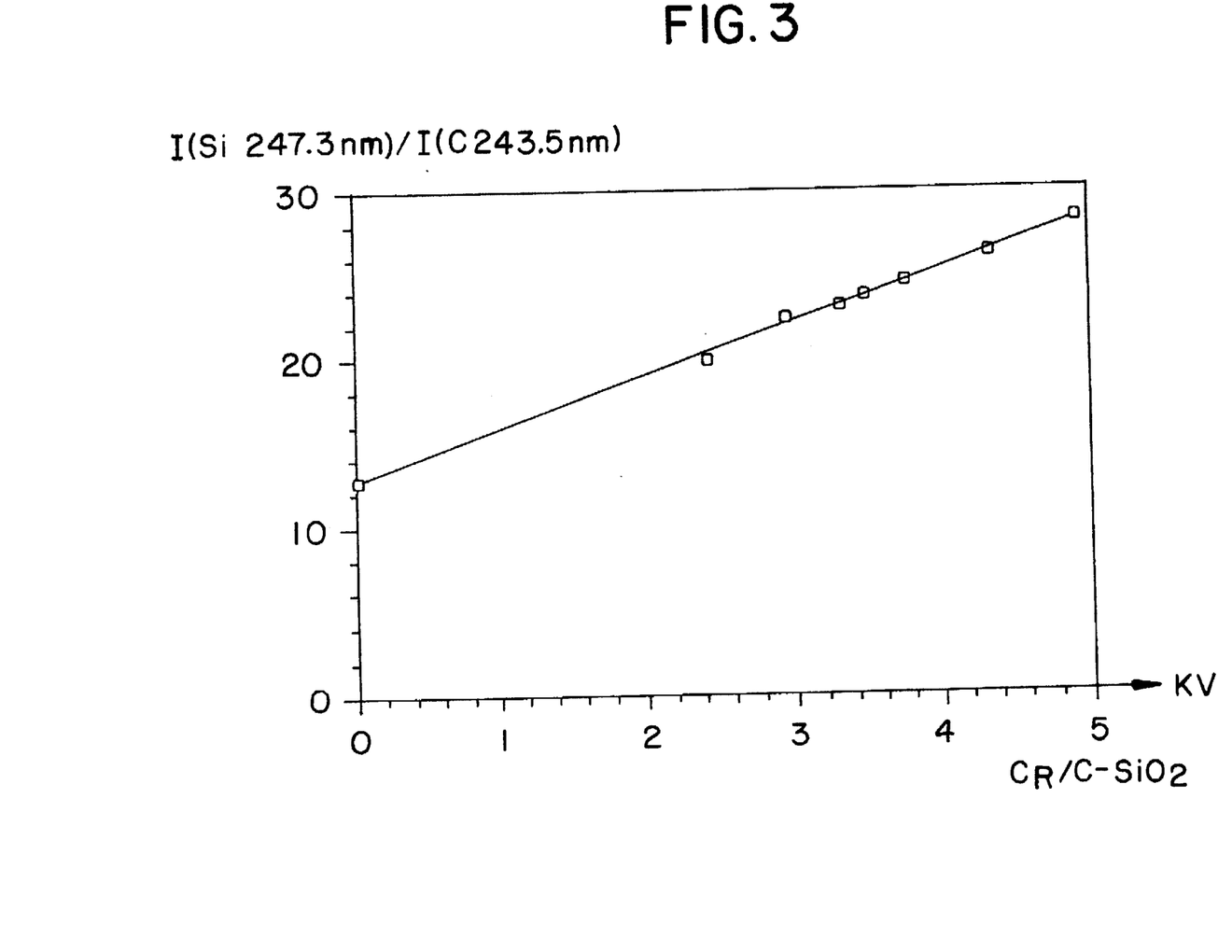
FIG. 3 is a graphic plot showing, by way of example, a calibration curve produced using spectral lines of FIG. 2, which curve was obtained by reference to specimens of known composition and is used to determine carbon black concentration in an evaluation of a second measurement of this invention.

FIG. 3 shows a calibration curve which plots the intensity ratio value between carbon (spectral line C=247.9 nm) and by way of example Si (spectral line Si=243.5 nm) against the concentration ratio KV between carbon black ($c_R$) and SiO$_2$ (c-SiO$_2$). Merely for reasons of clarity the intensity ratio I and the concentration ratio KV are defined as reciprocals of the relevant ratio according to FIG. 2.

By reference to the calibration curve according to FIG. 3 and from the intensity values for the elements C and Si obtained during the second measurement the magnitude of the appurtenant concentration ratio KV ($c_R$/c-SiO$_2$) can be obtained and from this the concentration value $C_R$ can be derived, insofar as the concentration value c-SiO$_2$ has already (as explained above) been determined by reference to the first measurement and the appurtenant corresponding calibration curve.

As the concentration values of further analysis elements can also be calculated from the values of the first measurement including the appurtenant calibration information, the second measurement—insofar as it extends to further analysis elements and corresponding appurtenant calibration curves are available for evaluation—can be used to determine the carbon black concentration from the corresponding ratio values for the other analysis elements as it were in a different way as verification. In this way it is also possible within the framework of the invention to derive a mean value from several determined carbon black concentration values which is used as a basis for determining the concentration value curve for carbon black in the particular surface section. To ensure that as consistent as possible process parameters are observed it is expedient to proceed in such a way that with both in each case connected measurements—as when determining the calibration information—the intensities of the same spectral lines of the reference element and of the analysis elements under consideration are used.

The plasmas for the first and the second measurements can in particular also be actuated simultaneously; this requires the use of two laser units, whose laser beams impinge on separate measuring points; the appurtenant plasmas—as already mentioned—are measured and analyzed with different, fixed time delays $t_{V1}$ and $t_{V2}$. The embodiment under consideration also requires that each of the two laser units is equipped with the facilities which permit the detection and analysis of the produced plasmas; therefore, as well as the required optical assemblies and deflector units for each laser beam there also have to be available in particular two spectrographs and two multichannel analyzers connected jointly with a computer serving as evaluator.

Within the framework of the invention it is also possible to bombard one and the same measuring point for the first and second measurements with several consecutive laser beams. From the intensity values of the plasmas of the appurtenant first and the appurtenant second plasma group a mean value can in each case be formed which can be used as a basis for determining the concentration values of the reference element, the analysis elements under consideration and the carbon black concentration.

Figure 4:
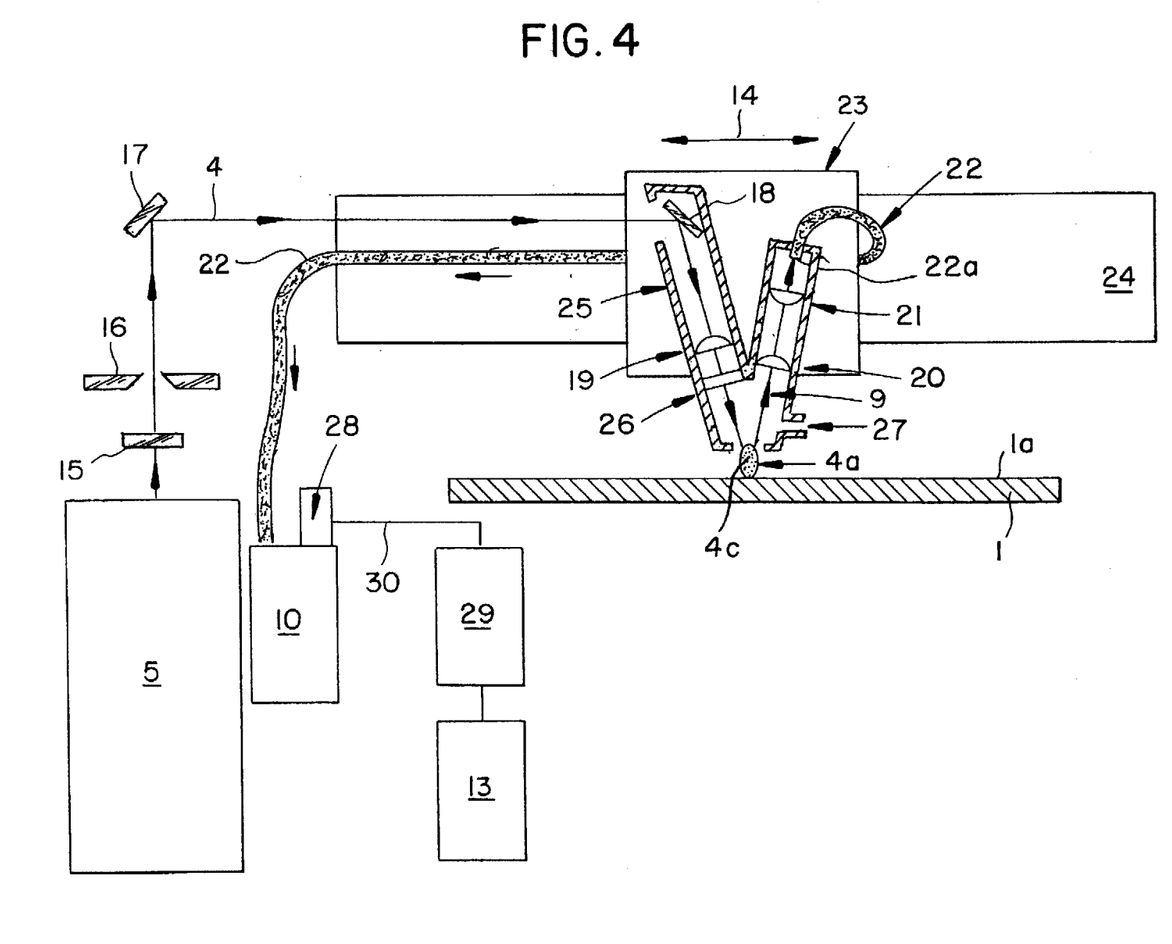
FIG. 4 is a side schematic view, partially cutaway, showing a device suitable for performing the process of this invention.

An embodiment example of a device suitable for the performance of the process is described in the following with reference to the representation in FIG. 4.

To determine the carbon black concentration and the compilation of the appurtenant concentration value curve the surface of the rubber slab 1 is scanned by such means that the end region 4a of a laser beam 4 is reciprocated in the direction of double arrow 14 (parallel to the drawing plane) during the measuring processes; while this is taking place the rubber slab 1 (as also indicated in FIG. 1) performs a continuous movement perpendicular to the drawing plane. The laser beam 4 emerging with variable pulse frequency from the laser unit 5 passes through an attenuating element 15, with which the laser beam intensity can be adjustable attenuated, and a beam aperture 16 with adjustable cross section and is focused by deflector mirrors 17 and 18 and a plane-convex lens 19 onto the surface 1a of the rubber slab where it produces the plasma 4c.

The characteristic radiation 9 emitted by the latter is focused by means of two plane-convex lenses 20, 21 onto the entry surface 22a of an optical fibre bundle 22. The optical elements 18 to 21 are mounted on a support frame 23 which in turn is guided—movably in the direction of the double arrow 14—on a support 24. A gas-tight housing 25 accommodating the optical elements 18 to 21 and exhibiting a shutter window 26 in the area between the plane-convex lens 19 and the surface 1a permits the performance of the measuring processes under protective gas (for example argon or compressed air); the latter can be introduced into the housing 25 through a supply connection 27 below the shutter window 26 and permits the performance of undistorted measurements even in dusty environments. Through the supply of inert gas to the housing (particularly in the case of measurements concerning sulphur) the disruptive oxygen can be displaced from the beam path of the plasma light.

The radiation emanating from the plasma 4c passes through the optical fibre bundle 22 into the inlet opening of the spectrograph 10, where it is spectrally dispersed and imaged onto the array detector of a multichannel analyzer 28 arranged in front of the focal plane of the spectrograph. The array detector (of the detector unit 12 in FIG. 1) permits the simultaneous measurement of a spectral region of the radiation from the plasma and thus allows multi-element analysis. The measurements to determine the intensity values of the constituents of interest in the surface 1a are carried out resolved in time. For this, the array detector of the multichannel analyzer 28 is actuated with a time delay relative to the particular laser pulse and is exposed for a short period of time. To adjust and actuate the time delay and exposure time ($t_{V1}$, $t_{V2}$ and $t_{B1}$, $t_{B2}$ for the first and second measurements respectively) there is a control unit 29 which controls the multichannel analyzer 28 via a control line 30. Control of the time sequences and evaluation of the measured spectra is effected by the computer 13. The latter also permits the time delay and the exposure time to be adjusted electronically to new values.

The invention is based on the hypothesis that the carbon black in the rubber compounds of interest here is only very weakly bound and is therefore immediately liberated by laser beam bombardment, heated in the plasma of the ambient atmosphere and stimulated to radiate. By contrast, the other evaporated constituents of the surface serving as specimen reach the plasma only relatively late, i.e. after around 1 µs; the carbon radiation resulting therefrom is weakened by absorption in the already existing carbon black cloud in front of the material surface, the weakening being the more pronounced the denser the carbon black cloud (i.e. the greater the carbon black concentration in the surface) is. Through appropriate selection of the observation period the two aforementioned radiation processes can be separated from one another. As, among other things, two independent contents—namely the concentration of total carbon and of carbon black—are each to be determined via the intensity of one carbon spectral line, the basic idea of the invention consists in determining the carbon black concentration by means of two laser pulses or laser pulse groups via two connected measurements of spectral intensities, namely a first measurement for a first plasma or a first plasma group and a second measurement for a second plasma or a second plasma group; related to the actuation of the particular laser pulse these two measurements will be carried out each with a fixed, different time delay relative to the respective time of actuation.

The time delay is adjustable within the framework of the invention; however, from the point of view of maintaining consistent process conditions for the measurements of a specific measurement series it is fixed. By way of the first measurement the intensities of the spectral lines of carbon as reference element ($I_C$) and at least approximately all other analysis elements ($I_{A,n}$) in the relevant surface section are determined and from these the appurtenant intensity ratios ($I_{A,n}/I_C$) of the spectral line of each analysis element to the spectral line of the reference element are determined.

By way of the second measurement the intensities of the spectral lines of the reference element ($I_C$) and at least one of the other analysis elements ($I_{A,n}$) are determined and from these the appurtenant intensity ratio in each case is determined, this measurement being carried out with a shorter delay time than the appurtenant first measurement. To evaluate the results of the first and second measurements use is made of calibration curves obtained by reference to specimens of known composition and by measurements with the time delay of the first and second measurements; these calibration curves show the relationship between the intensity ratio values and the concentration ratio of the particular constituents [$I_{A,n}/I_C = f(c_{A,n}/c_C)$ and $I_{A,n}/I_C = f(c_{A,n}/c_R)$].

By comparison with the calibration curve data it is possible by way of the intensity ratio values from the first measurement to determine the values of the appurtenant concentration ratios of at least approximately all analysis elements in the particular surface section and from these the value for the concentration of the reference element, from which the magnitude of the concentration of individual analysis elements can also be derived. Determining the concentration of the reference element requires that the concentration of all constituents in the surface amounts to 100% or differs only negligibly from this value or the balance of the concentration is sufficiently precisely known.

By comparison with the data of at least one further calibration curve and using the appurtenant intensity ratio value from the second measurement the value of the concentration ratio between carbon black ($c_R$) and the particular analysis element ($c_{A,n}$) is determined and taking into account the previously calculated magnitude of the concentration of this analysis element the magnitude of the carbon black concentration is derived. The result of the second measurement is thus in each case evaluated taking into account the result of the appurtenant first measurement—which permits determination of the magnitude of the concentration of total carbon as well as that of selected or all other analysis elements in the surface—in such a way that the magnitude of the carbon black concentration ($c_R$) is derived from at least one intensity ratio value obtained by the second measurement, the concentration ratio value resulting from the appurtenant calibration curve and knowledge of the concentration of the analysis element, which concentration forms part of the aforementioned concentration ratio value.

The calibration curves are obtained using standard specimens, i.e. specimens of known composition, with carbon being used as reference element (i.e. as internal standard) for rubber compounds, particularly for tire compounds. Within the framework of the invention, however, other reference elements can also be used. In addition the invention can fundamentally also be used to determine other constituents which are present in different forms and under laser beam bombardment behave differently like carbon black and the carbon assigned to the other constituents of the material. Rubber compounds for tires consist of 70% to 85% carbon; up to 50% of the carbon can be assigned to the added carbon black.

Because the measuring process is time-resolved, i.e. takes place in a certain period after actuation of the particular laser pulse, the carbon black-carbon can be distinguished from the total carbon by optical means (e.g. by means of a multi-channel analyzer) and its concentration in the surface to be examined can thus be determined.

The process is preferably configured such that the delay time after which the second measurement is carried out in each case is between 0.1 and 0.5 µs and/or the delay time for the first measurement is more than 0.5 to 5.0 µs.

The exposure time for identifying the produced plasma during the second measurement should be between 0.1 and 0.3 µs and the exposure time for identifying the produced plasma during the first measurement should be between 0.2 and 10 µs. The aforementioned exposure times show that the exposure time assigned to the first measurement should generally be greater (where necessary also considerably greater) than the exposure time assigned to the second measurement.

With a view to maintaining as consistent measuring conditions as possible the process is preferably carried out such that with both measurements—to the extent necessary for determining the carbon black concentration—the intensities of the same spectral lines of the reference element and the analysis elements are measured in each case.

As the carbon black concentration is determined by reference to the evaluation of the appurtenant first measurement, a multiple calculation can also be carried out on the basis of the known concentration values of different analysis elements and a mean value for the carbon black concentration can be derived in each case which is used as a basis for determining the concentration value curve.

With regard to the actuation of the laser pulses relative to the surface the invention can be configured in different ways, i.e. the plasmas for the first and the second measurements can be produced separately from one another in space and/or time.

Separation in time can be effected—as for example in the case of the object of the previously cited DE-A1-40 04 627—by such means that the plasmas for the first and the second measurements are produced consecutively in time by one and the same laser unit.

Spatially separate plasmas can be produced by for example two laser pulses being actuated simultaneously in each case by two laser units; the two laser units can however also be switched such that the two laser pulses are produced at different times.

Finally, two laser units for producing lasers pulses for the first and second measurements can also be arranged and switched in such a way that the two connected laser beam focuses impinge consecutively on one measuring point.

The process can further be configured in such a way that several plasmas are produced for the first and second measurements in each measuring point. From the intensity values of the plasmas of each plasma group a mean value for the intensity value can be formed which is used as a basis for determining the concentration values for the reference element, the selected or other analysis elements and the carbon black.

The basic idea of this configuration thus consists in bombarding one and the same measuring point for the first and the second measurements with several consecutive laser pulses in each case; in this way information can also be gained which is not restricted only directly to the surface of the material to be examined.

The device is characterized in that each detector unit can be controlled with an adjustable time delay such that two measurements of the spectral intensities of separately produced plasmas are carried out each with a fixed, different time delay relative to the actuation time of the particular laser pulse; the time delay for the second measurement—by means of which the spectral line intensities of the reference element carbon ($I_C$) and at least one of the other analysis elements ($I_{A,n'}$) in the surface section can be ascertained—is smaller than that of the first measurement for determining the spectral line intensities of the reference element ($I_C$) and at least approximately all other analysis elements ($I_{A,n}$).

In the computer connected with the at least one detector unit is stored calibration information which is based on reference measurements carried out with the time delay of both the first and the second measurement on specimens of known composition and which shows the magnitude of the concentration ratio of the other analysis elements or the at least one analysis element to the reference element as a function of the appurtenant intensity ratio values.

The computer is configured such that from the intensity values of the first and second measurements ratio values corresponding to the calibration information are formed, and by comparison with the latter first the concentration of total carbon ($c_C$) and that of the at least one selected analysis element ($c_{A,n}$) and then by reference to the known concentration value ($c_{A,n}$) of at least one analysis element the magnitude of the carbon black concentration ($c_R$) are determined, the latter being used to establish the concentration value curve.

The device can further be configured such that the laser pulses can be actuated relative to the surface such that the appurtenant plasmas for the first and the second measurements are produced separately from each other in space and/or in time (claim 11). To this end the facility to produce the laser beams may also exhibit several laser units.

Particularly for determining the carbon black concentration and carbon black distribution in plates an embodiment is suitable by means of which several laser pulses can be accumulated. For the first and the second measurements in an appurtenant first and second measuring point several laser pulses can be actuated in each case and from the intensity values of the first and the second plasma groups a mean value is formed in each case which forms the starting value for determining the concentration values.

The device is preferably configured and designed such that the time delay for performing the first and the second measurements and the appurtenant exposure time for registering the produced plasma during the performance of the first and the second measurements are steplessly variable. It has proved advantageous to set the delay time for the two measurements between more than 0.5 and 5.0 μs and 0.1 and 0.5 μs respectively and the exposure time between 0.2 and 10 μs and 0.1 and 0.3 μs respectively.

We claim:

1. Process for manufacturing pneumatic tire for vehicle wheels, comprising the steps of:

preparing at least one rubber compound by mixing together at least one polymeric material with other ingredients, including carbon black, according to prefixed quantitative ratios between said ingredients established in a given recipe;

forming from said rubber compound at least one semi-finished component for said tire;

assembling together a plurality of said semi-finished components to build up a raw carcass to be molded and vulcanized in a curing mold, wherein this process further comprises the steps of:

quantitatively detecting, on-line, the quantity of carbon black contained in said at least one rubber compound to thereby monitor in real time a dispersion degree and a homogeneity of the carbon black in said rubber compound, by taking respective first and second measurements:

wherein each of the first and second measurements is made by directing a laser of a laser apparatus at the rubber compound to thereby produce a plasma, detecting radiation from the plasma, producing a spectrum from the radiation, measuring intensities of spectral lines of the spectrum;

and wherein, in said first measurement, said measuring of said intensities of said spectral lines is carried out at a first time delay from actuation of the laser apparatus for causing the plasma whose radiation is measured in the first measurement, and in said first measurement, the intensities of spectral lines of carbon and at least approximately all other analysis constituents of the rubber compound forming the spectrum are measured; and in said second measurement, the measuring of said intensities of said spectral lines is carried out at a second time delay from actuation of the laser apparatus for causing the plasma whose radiation is being measured in the second measurement, with the first and second time delays for the first and second measurements being substantially different from one another and, in the second measurement, the spectral lines of carbon and at least one of the other analysis constituents is measured;

determining the quantity of carbon black in said at least one rubber compound using the intensities measured in the first and second measurements, in conjunction with stored values of intensities of known rubber compound samples;

controlling the quantity of carbon black which is being mixed into said polymeric material during said mixing step, by using said on-line detection of carbon black to achieve the prefixed quantitative ratios of ingredients.

2. Process as in claim 1 wherein the first time delay is longer than said second time delay so that the intensity of a carbon spectral line for the second measurement is determined to a greater degree by carbon black in the rubber compound than in the first measurement.

3. Process as in claim 2 wherein the step of determining the quantity of carbon black is carried out by the following substeps:

comparing ratios of intensities of spectral lines measured in the first measurement with first stored values, which first stored values are for calibration curves obtained by carrying out measurements like those of the first measurement with a similar first time delay but on specimens of known compositions, for determining a value of the concentration of carbon in the rubber compound as well as the concentration of at least one additional constituent;

comparing ratios of intensities of spectral lines measured in the second measurement with second stored values, which second stored values are for a calibration curve obtained by carrying out similar measurements like those of the second measurement, with a similar second time delay, but on specimens of known compositions for determining a value of a concentration ratio between carbon black and the at least one additional constituent and, using the previously determined magnitude of the concentration of the additional constituent, deriving a magnitude of a carbon black concentration.

* * * * *